(12) United States Patent
Barton et al.

(10) Patent No.: US 9,150,479 B1
(45) Date of Patent: Oct. 6, 2015

(54) CATALYSTS AND METHODS FOR ALCOHOL DEHYDRATION

(71) Applicant: Dow Global Technologies LLC, Midland, MI (US)

(72) Inventors: David G. Barton, Midland, MI (US); Adam Chojecki, Ghent (BE); Paul R. Elowe, Midland, MI (US); Beata A. Kilos, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/385,917

(22) PCT Filed: May 29, 2013

(86) PCT No.: PCT/US2013/043092
§ 371 (c)(1),
(2) Date: Sep. 17, 2014

(87) PCT Pub. No.: WO2013/181238
PCT Pub. Date: Dec. 5, 2013

Related U.S. Application Data

(60) Provisional application No. 61/653,494, filed on May 31, 2012.

(51) Int. Cl.
*C07C 41/09* (2006.01)
*C09K 5/10* (2006.01)
*C09K 5/00* (2006.01)

(52) U.S. Cl.
CPC .. *C07C 41/09* (2013.01); *C09K 5/00* (2013.01)

(58) Field of Classification Search
CPC ................................. C07C 41/09; C09K 5/10
USPC ..................................... 568/635, 645; 252/73
See application file for complete search history.

(56) References Cited

U.S. PATENT DOCUMENTS

| 3,922,331 A | 11/1975 | MacDonald et al. |
| 4,156,698 A | 5/1979 | Dwyer et al. |
| 5,925,798 A | 7/1999 | Gambell et al. |

FOREIGN PATENT DOCUMENTS

| EP | 0317208 | 5/1989 |
| EP | 0584415 | 3/1994 |
| WO | 200015730 | 3/2000 |
| WO | 2002060818 | 8/2002 |

OTHER PUBLICATIONS

Chemistry International—Newsmagazine for IUPAC, Chinese Terms for Chemical Elements, Chang Hao, IUPAC publications, 2004, pp. 1-6.
Nomenclature of Inorganic Chemistry, IUPAC Recommendations 2005, RSC Publishing 2005, pp. 1-377.

*Primary Examiner* — Sikarl Witherspoon
(74) *Attorney, Agent, or Firm* — Steven W. Mork

(57) ABSTRACT

Provided is a process for preparing a diaryl ether compound through the dehydration of an aromatic alcohol compound in the presence of a dehydration catalyst. The dehydration catalyst is an oxide of a heavy rare earth element, wherein the heavy rare earth element is terbium, dysprosium, holmium, erbium, thulium, ytterbium, lutetium, or mixtures thereof.

10 Claims, No Drawings

_US 9,150,479 B1_

CATALYSTS AND METHODS FOR ALCOHOL DEHYDRATION

CROSS-REFERENCE TO RELATED APPLICATIONS

This application claims priority from provisional application Ser. No. 61/653,494, filed May 31, 2012, which is incorporated herein by reference in its entirety.

BACKGROUND

This invention relates generally to catalysts and methods for the dehydration of aromatic alcohol compounds to ethers. More particularly, the invention uses a dehydration catalyst comprising an oxide of a heavy rare earth element for the dehydration of aromatic alcohol compounds to diaryl ethers.

Diaryl ethers are an important class of industrial materials. Diphenyl oxide (DPO), for instance, has many uses, most notably as the major component of the eutectic mixture of DPO and biphenyl, which is the standard heat transfer fluid for the concentrating solar power (CSP) industry. With the current boom in CSP has come a tightening of the supply of DPO globally and questions surrounding the sustainability of the technology have arisen.

Diaryl ethers are currently manufactured commercially via two major routes: reaction of a haloaryl compound with an aryl alcohol; or gas-phase dehydration of an aryl alcohol. The first route, for example where chlorobenzene reacts with phenol in the presence of caustic and a copper catalyst, typically leads to less pure product and requires high pressure (5000 psig), uses an expensive alloy reactor and produces stoichiometric quantities of sodium chloride.

The second route, which is a more desirable approach, accounts for the largest volume of diaryl ethers produced but requires a very active and selective catalytic material. For instance, DPO can be manufactured by the gas-phase dehydration of phenol over a thorium oxide (thoria) catalyst (e.g., U.S. Pat. No. 5,925,798). A major drawback of thoria however is its radioactive nature, which makes its handling difficult and potentially costly. Furthermore, the supply of thoria globally has been largely unavailable in recent years putting at risk existing DPO manufacturers utilizing this technology. Additionally, other catalysts for the gas-phase dehydration of phenol, such as zeolite catalysts, titanium oxide, zirconium oxide and tungsten oxide, generally suffer from lower activity, significantly higher impurity content and fast catalyst deactivation.

With a chronic shortage of diaryl ethers such as DPO in sight and a pressing need to increase capacity, it has become crucial to develop alternate methods to produce such materials in a cost-effective and sustainable manner.

The problem addressed by this invention, therefore, is the provision of new catalysts and methods for manufacture of diaryl ethers from aryl alcohol compounds.

STATEMENT OF INVENTION

We have now found that a catalyst comprising an oxide of a heavy rare earth element is effective for the preparation of diaryl ethers from aromatic alcohol compounds. Advantageously, the catalyst exhibits remarkable selectivity for the desired product. Moreover, the catalyst is non-radioactive. This invention, therefore, represents a unique solution for diaryl ether supply issues globally.

In one aspect, there is provided a method for preparing a diaryl ether, the method comprising dehydrating an aromatic alcohol compound over a dehydration catalyst, wherein the dehydration catalyst is an oxide of a heavy rare earth element.

In another aspect, there is provided a method for producing a heat transfer fluid, the method comprising: preparing a diaryl ether by contacting an aromatic alcohol compound with a dehydration catalyst, wherein the dehydration catalyst is an oxide of a heavy rare earth element; isolating the diaryl ether from the dehydration catalyst; and mixing the isolated diaryl ether with biphenyl, wherein the mixture forms a eutectic mixture.

DETAILED DESCRIPTION

Unless otherwise indicated, numeric ranges, for instance as in "from 2 to 10," are inclusive of the numbers defining the range (e.g., 2 and 10).

Unless otherwise indicated, ratios, percentages, parts, and the like are by weight.

As noted above, in one aspect the invention provides a method for producing a diaryl ether by dehydrating an aromatic alcohol compound over an oxide of a heavy rare earth element. It has been discovered that such catalysts exhibit high selectivity for the desired diaryl ether compounds with relatively low formation of undesirable byproducts. For instance, as demonstrated by the examples, in the synthesis of diphenyl oxide from phenol, a selectivity for the DPO of 50% or greater may be achieved. In some embodiments, a selectivity of 80% or greater may be achieved. In some embodiments, a selectivity of 90% or greater, or alternatively 95% or greater is possible.

In addition to being highly selective, the catalysts are further advantaged because they are non-radioactive, thus eliminating the safety and environmental issues, as well as higher costs, associated with the handling of radioactive materials, such as the thoria catalysts of the prior art.

The dehydration catalyst of the invention comprises an oxide of a heavy rare earth element. By a "heavy rare earth element" is meant terbium, dysprosium, holmium, erbium, thulium, ytterbium, lutetium, or mixtures thereof. By "oxide of heavy rare earth element" is meant a compound that contains at least one oxygen-heavy rare earth element bond. Examples include, but are not limited to, $Tb_2O_3$, $Tb_4O_7$, $TbO_2$, $Tb_6O_{11}$, $Dy_2O_3$, $Ho_2O_3$, $Er_2O_3$, $Tm_2O_3$, $Yb_2O_3$, and $Lu_2O_3$.

In some embodiments, the catalyst is an oxide of terbium. In some embodiments, the catalyst is an oxide of dysprosium In some embodiments, the catalyst is an oxide of holmium. In some embodiments, the catalyst is an oxide of erbium. In some embodiments, the catalyst is an oxide of thulium. In some embodiments, the catalyst is an oxide of ytterbium. In some embodiments, the catalyst is an oxide of lutetium. Mixtures of oxides, such as mixtures of oxides of one heavy rare earth element, or mixtures of oxides of two or more different heavy rare earth elements, are also encompassed by the invention.

The catalyst may optionally contain other atoms, such as halogens, including chloride or fluoride. In some embodiments, a preferred catalyst for use in the invention contains a heavy rare earth element, oxygen and chlorine atoms. In some embodiments, the catalyst comprises, in addition to the heavy rare earth element and oxygen, chlorine in an amount of less than 40 weight percent, alternatively 30 weight percent or less, alternatively 17 weight percent or less, alternatively 10 weight percent or less, or alternatively 2 weight percent or less. In some embodiments, the catalyst comprises the chlorine in an amount of at least 0.001 weight percent, alternatively at least 0.1 weight percent, alternatively at least 1 weight percent, or alternatively at least 2 weight percent. In some embodiments, the catalyst contains between 1 and 17 weight percent chlorine. The chlorine is in the form of chloride ion (Cl⁻). Non limiting examples of suitable compounds may include terbium oxychloride, dysprosium oxychloride, holmium oxychloride, erbium oxychloride, thulium oxychloride, ytterbium oxychloride, lutetium oxychloride, or an oxide of the heavy rare earth element also containing a chloride (e.g., from $NH_4Cl$, HCl, etc., or from chloride containing heavy rare earth element precursors). By "oxychloride" is meant a compound that contains metal-oxygen and metal-chlorine bonds. Examples further include, again without limitation, heavy rare earth element oxide catalysts based on chlorate oxyanions, such as hypochlorite (ClO⁻); chlorite ($ClO_2^-$); chlorate ($ClO_3^-$), perchlorate ($ClO_4^-$) where Cl is oxidized (+2, +3, +4, +5), as well as amorphous materials.

Catalysts suitable for use in the invention may be prepared by those skilled in the art or they may be purchased from commercial vendors.

The catalyst may optionally contain a binder and/or matrix material that is different from the active oxide of the heavy rare earth element. Non-limiting examples of binders that are useful alone or in combination include various types of hydrated alumina, silicas and/or other inorganic oxide sols, and carbon. Upon heating, the inorganic oxide sol, preferably having a low viscosity, is converted into an inorganic oxide binder component.

Where the catalyst composition contains a matrix material, this is preferably different from the active catalyst and any binder. Non-limiting examples of matrix materials include clays or clay-type compositions.

The catalyst, including any binder or matrix materials, may be unsupported or supported. Non-limiting examples of suitable support materials include titania, alumina, zirconia, silica, carbons, zeolites, magnesium oxide, and mixtures thereof. Where the catalyst contains a binder, matrix or support material, the amount of oxide of heavy rare earth element (the active component of the catalyst) may be between 1 and 99 percent by weight based on the total weight of the catalyst (including the oxide, and any support, binder or matrix materials).

The catalyst may be formed into various shapes and sizes for ease of handling. For instance, the catalyst (plus any binder, matrix, or support) may be in the form of pellets, spheres, or other shapes used in the industry.

Aromatic alcohol compounds suitable for use in the process of this invention include aromatic compounds containing at least one alcohol group and one, two, three or more aromatic moieties. Suitable compounds include phenols and α- and β-hydroxy-substituted fused aromatic ring systems. Apart from the hydroxy substituent, the compounds may be unsubstituted, as in phenol or naphthol. Optionally, however, the compounds may be further substituted with at least one alkyl group containing from 1 to about 10 carbon atoms, preferably, from 1 to 3 carbon atoms, or substituted with at least one alternative substituent which is inert to the dehydration coupling reaction. Suitable inert substituents include cyano, amino, nitro, carboxylic acid (e.g., $C_0$-$C_6$—COOH), ester, $C_6$-$C_{12}$ aryl, $C_2$-$C_6$ alkenyl, alkyloxy, aryloxy, and phenoxy moieties. It is also possible for the aromatic alcohol compound to be substituted with both an alkyl substituent and one of the alternative inert substituents. Each of the aforementioned alkyl substituents and/or alternative inert substituents is attached preferably to an aromatic ring carbon atom which is located in an ortho, meta or para position relative to the hydroxy moiety. Optionally, the alkyl substituent may contain from 3 to 4 carbon atoms, and in combination with a phenol or fused aromatic ring system may form a saturated ring fused to the aromatic ring. An acceptable feed may contain a mixture of aromatic alcohols, including mixtures of the foregoing.

Non-limiting examples of suitable phenols include unsubstituted phenol, m-cresol, p-cresol, 3,4-xylenol, 3,5-xylenol, and 3,4,5-trimethylphenol. Other suitable phenols include compounds corresponding to the above-mentioned examples except that one or more of the methyl substituents are replaced by an ethyl, propyl or butyl substituent. Non-limiting examples of α- and β-hydroxy-substituted fused aromatic ring systems include α- and β-naphthol and 5-tetralinol. Other non-limiting examples of aromatic alcohols include benzenediols (catechol, resorcinol or hydroquinone), o-cresol, o-phenylphenol, m-phenylphenol or p-phenylphenol. One skilled in the art may find other phenols and α- and β-hydroxy-substituted fused aromatic ring systems which are also suitable for the purposes of this invention. Preferably, the aromatic alcohol is unsubstituted phenol or a substituted phenol wherein the substituent is methyl, ethyl or hydroxyl. More preferably, the aromatic alcohol is unsubstituted phenol, cresol or a benzenediol. Most preferably, the aromatic alcohol is unsubstituted phenol.

According to the method of the invention for preparing a diaryl ether, a dehydration catalyst as described herein is contacted with the aromatic alcohol compound. The contacting of the catalyst with the aromatic alcohol compound is carried out under reaction conditions such that the diaryl ether is formed.

The catalyst is contacted with the aromatic alcohol compound either in the gas phase or in the liquid phase. In addition, the aromatic alcohol may be diluted with a diluent or it may be neat. Suitable diluents include, without limitation, nitrogen, argon, water vapor, water, oxygen or hydrogen. When a diluent is used, the concentration of the aromatic alcohol compound may be, for instance, 1 volume percent or greater and less than 100 volume percent.

In a preferred embodiment, the aromatic alcohol is contacted with the catalyst in the gas phase. Typically, the aromatic alcohol is introduced into a reactor containing the catalyst at elevated temperature, for instance, between 200 and 800° C., alternatively between 300 and 600° C., alternatively between 400 and 600° C., or alternatively between 450 and 550° C. The reaction may be conducted at atmospheric pressure, under reduced pressure, or at elevated pressure such as up to 5000 psi. In some embodiments, atmospheric pressure or slightly above (e.g., up to about 50 psi) is preferred. In some embodiments, the gas flow rate of the aromatic alcohol over the catalyst (weighted hourly space velocity or WHSV) is from 0.01 to 100 grams per hour per gram (g/g·h). In some embodiments, WHSV is from 0.1 to 20 g/g·h, alternatively 0.1 to 5 g/g·h, or alternatively 0.1 to 1 g/g·h.

In some embodiments, it may be useful to subject the reactor to startup conditions which may provide various benefits, such as prolonging catalyst life. Suitable startup condition include, for example, exposing the catalyst to dilute amounts of the aromatic alcohol at lower temperature before changing to full operating conditions as described above and demonstrated by the examples.

Following the reaction, the diaryl ether product is recovered from the catalyst and optionally further purified. Unreacted alcohol and other reaction by-products may be separated using methods known in the art. Such methods include but are not limited to distillation, crystal refining, simulated moving bed technique or a combination thereof.

In some embodiments, the diaryl ether prepared by the process of the invention is diphenyl oxide (DPO). Other diaryl ether compounds that may be prepared by the process of the invention include, without limitation, compounds containing at least one ether functionality whereby two aryl moieties are connected by an oxygen atom (Ar—O—Ar'), including polyaryl compounds and compounds prepared from the aromatic alcohols described above. Specific examples include, but are not limited to, phenoxytoluene isomers, including 3-phenoxytoluene, ditolyl ether isomers, polyphenyl ethers (PPEs), biphenylphenyl ether isomers and naphthyl phenyl ethers.

The diaryl ethers prepared by the invention are useful in a variety of applications, including as high temperature solvents, as intermediates in preparing flame retardants and surfactants, and as components in heat transfer fluids. Furthermore, certain diaryl ethers prepared by the invention are useful as high performance lubricants and as intermediates in preparing pyrethroid insecticides.

In some embodiments, a preferred use of the diaryl ether is in high temperature heat transfer fluids. High temperature heat transfer fluids may be prepared by making the diaryl ether according to the process described above and then mixing the diaryl ether with biphenyl. The amounts necessary to provide a suitable fluid can be readily determined by a person with ordinary skill in the art. For diphenyl oxide and biphenyl, the amount of DPO may be, for instance, from 70 to 75 weight percent based on the total weight of the DPO and biphenyl. A preferred amount of DPO is that required to form a eutectic mixture with the biphenyl, which is about 73.5 weight percent based on the total weight of the DPO and biphenyl.

Some embodiments of the invention will now be described in detail in the following Examples.

EXAMPLES

Example 1

Holmium(III) oxide is used for the conversion of phenol to diphenyl oxide (DPO). The powder is pressed and sieved to obtain particles that are between 0.60 mm and 0.85 mm in diameter. The particles are loaded into an electrically heated stainless steel reactor tube and heated to the reaction temperature with nitrogen flowing through the tube. After the reaction temperature is reached, vapor-phase phenol is passed through the reactor tube. The conversion of phenol is carried out at a weighted hourly space velocities of 1 (WHSV=gram phenol/gram catalyst-hour) and at 500° C. Test conditions and results are shown in Table 1.

TABLE 1

| Test Conditions | Conversion [mol. %] phenol | Selectivity [mol. %] | | | | | |
|---|---|---|---|---|---|---|---|
| | | Diphenyl Oxide | OPP | DBF | O-BIPPE | M-BIPPE | P-BIPPE |
| T = 500° C. Feed: 33% PhOH, 67% N2 ToS = 1 hrs WHSV 1 hr$^{-1}$ | 0.11% | 48.63% | 0.90% | 50.47% | 0.00% | 0.00% | 0.00% |
| T = 500° C. Feed: 33% PhOH, 67% N2 ToS = 2 hrs WHSV 1 hr$^{-1}$ | 0.09% | 48.97% | 0.56% | 50.47% | 0.00% | 0.00% | 0.00% |
| T = 500° C. Feed: 33% PhOH, 67% N2 ToS = 5 hrs WHSV 1 hr$^{-1}$ | 0.06% | 51.51% | 0.20% | 48.29% | 0.00% | 0.00% | 0.00% |

OPP: orthophenylphenol
DBF: dibenzofuran
O-BIPPE: ortho-biphenylphenyl ether
M-BIPPE: meta-biphenylphenyl ether
P-BIPPE: para-biphenylphenyl ether
PhOH: phenol
N2: nitrogen
ToS: time on stream (ToS = 0 hours defined at start of phenol flow)

Example 2

The synthesis of the chlorided holmium oxide (Cl—Ho$_2$O$_3$) is carried out by a thermal decomposition of HoCl$_3$.6 H$_2$O. Thus, a sample of the powdered precursor (approximately 10 g) is calcined in air in a static calcination oven under the following temperature protocol: ramp 1.41° C./min to 550° C., dwell 3 hours at 550° C., cool down to room temperature. The chlorine content of the catalyst is assayed by XRF to 13.58 wt. % chlorine. The XRD data showed the presence of holmium oxychloride phases.

The catalyst is used in the dehydration of phenol. The powder is pressed and sieved to obtain particles that are between 0.60 mm and 0.85 mm in diameter. The particles are loaded into an electrically heated stainless steel reactor tube and heated to the reaction temperature with nitrogen flowing through the tube. After the reaction temperature is reached, vapor-phase phenol is passed through the reactor tube. The conversion of phenol is carried out at a weighted hourly space velocities of 1 (WHSV=gram phenol/gram catalyst·hour) and at 500° C. Test conditions and results are shown in Table 2.

TABLE 2

| Test Conditions | Conversion [mol. %] Phenol | Selectivity [mol. %] | | | | | |
|---|---|---|---|---|---|---|---|
| | | Diphenyl Oxide | OPP | DBF | O-BIPPE | M-BIPPE | P-BIPPE |
| T = 500° C. Feed: PhOH ToS = 2.25 hrs WHSV 1 hr$^{-1}$ | 1.23% | 92.68% | 0.31% | 7.01% | 0.00% | 0.00% | 0.00% |
| T = 500° C. Feed: PhOH ToS = 3.25 hrs WHSV 1 hr$^{-1}$ | 1.36% | 91.33% | 0.31% | 8.37% | 0.00% | 0.00% | 0.00% |
| T = 500° C. Feed: PhOH ToS = 4.25 hrs WHSV 1 hr$^{-1}$ | 1.57% | 88.91% | 0.17% | 10.91% | 0.00% | 0.00% | 0.00% |
| T = 500° C. Feed: PhOH ToS = 5.5 hrs WHSV 1 hr$^{-1}$ | 1.45% | 87.46% | 0.40% | 12.14% | 0.00% | 0.00% | 0.00% |

Example 3

A 1M DyCl$_3$ solution, prepared by dissolving 18.849 g DyCl$_3$ in 50 mL DI H$_2$O, is added dropwise along with tetrapropylammonium hydroxide (76.261 g, from a 40 wt % TPAOH solution) over 15 min into a 600 mL beaker containing an initial 100 mL DI H$_2$O. The solution is stirred at 500 rpm on magnetic stir plate with a 3 inch stir bar. The resulting precipitate is allowed to age in solution for 1 h with stirring, after which it is centrifuged at 5000 rpm for 10 min. The decanted precipitate is placed into an oven, dried at 120° C. for 4 h and calcined at 500° C. for 4 h with a ramp rate of 5° C./min to yield 8.6 g of product.

Example 4

Catalytic evaluation of the catalyst from Example 3 is carried out using a similar procedure as in Example 2. Test conditions and results are shown in Table 3.

Example 5

A 1M YbCl$_3$ solution, prepared by dissolving 19.387 g YbCl$_3$ in 50 mL DI H$_2$O, is added dropwise along with tetrapropylammonium hydroxide (76.265 g, from a 40 wt % TPAOH solution) over 15 min into a 600 mL beaker containing an initial 100 mL DI H$_2$O. The solution is stirred at 500 rpm on magnetic stir plate with a 3 inch stir bar. The resulting precipitate is allowed to age in solution for 1 h with stirring, after which it is centrifuged at 5000 rpm for 10 min. The decanted precipitate is placed into an oven, dried at 120° C. for 4 h and calcined at 500° C. for 4 h with a ramp rate of 5° C./min to yield 9 g of product.

Example 6

Catalytic evaluation of the catalyst from Example 5 is carried out using a similar procedure as in Example 2. Test conditions and results are shown in Table 4.

TABLE 3

| Test Conditions | Conversion [mol. %] Phenol | Selectivity [mol. %] | | | | | |
|---|---|---|---|---|---|---|---|
| | | Diphenyl Oxide | OPP | DBF | O-BIPPE | M-BIPPE | P-BIPPE |
| T = 500° C. Feed: PhOH ToS = 1.25 hrs WHSV 1 hr$^{-1}$ | 8.30% | 96.11% | 0.01% | 3.61% | 0.00% | 0.14% | 0.14% |
| T = 500° C. Feed: PhOH ToS = 2.25 hrs WHSV 1 hr$^{-1}$ | 11.74% | 97.58% | 0.10% | 2.14% | 0.00% | 0.08% | 0.09% |
| T = 500° C. Feed: PhOH ToS = 3.75 hrs WHSV 1 hr$^{-1}$ | 6.36% | 96.68% | 0.25% | 2.79% | 0.00% | 0.11% | 0.16% |
| T = 500° C. Feed: PhOH ToS = 4.75 hrs WHSV 1 hr$^{-1}$ | 11.88% | 95.96% | 0.10% | 3.63% | 0.04% | 0.09% | 0.19% |

TABLE 4

| Test Conditions | Conversion [mol. %] Phenol | Selectivity [mol. %] | | | | | |
|---|---|---|---|---|---|---|---|
| | | Diphenyl Oxide | OPP | DBF | O-BIPPE | M-BIPPE | P-BIPPE |
| T = 500° C. Feed: PhOH ToS = 1.5 hrs WHSV 1 hr$^{-1}$ | 19.76% | 97.39% | 0.15% | 2.18% | 0.02% | 0.19% | 0.07% |
| T = 500° C. Feed: PhOH ToS = 2.5 hrs WHSV 1 hr$^{-1}$ | 22.20% | 97.53% | 0.06% | 2.20% | 0.02% | 0.14% | 0.06% |
| T = 500° C. Feed: PhOH ToS = 3 hrs WHSV 1 hr$^{-1}$ | 22.29% | 97.55% | 0.10% | 2.10% | 0.04% | 0.14% | 0.06% |

Example 7

A 1M ErCl$_3$ solution, prepared by dissolving 15.272 g ErCl$_3$ in 40 mL DI H$_2$O, is added dropwise along with tetrapropylammonium hydroxide (61.030 g, from a 40 wt % TPAOH solution) over 15 min into a 600 mL beaker containing an initial 100 mL DI H$_2$O. The solution is stirred at 500 rpm on magnetic stir plate with a 3 inch stir bar. The resulting precipitate is allowed to age in solution for 1 h with stirring, after which it is centrifuged at 5000 rpm for 10 min. The decanted precipitate is placed into an oven, dried at 120° C. for 4 h and calcined at 500° C. for 4 h with a ramp rate of 5° C./min to yield 7.4 g of product.

Example 8

Catalytic evaluation of the catalyst from Example 7 is carried out using a similar procedure as in Example 2. Test conditions and results are shown in Table 5.

TABLE 5

| Test Conditions | Conversion [mol. %] Phenol | Selectivity [mol. %] | | | | | |
|---|---|---|---|---|---|---|---|
| | | Diphenyl Oxide | OPP | DBF | O-BIPPE | M-BIPPE | P-BIPPE |
| T = 500° C. Feed: PhOH ToS = 4.5 hrs WHSV 1 hr$^{-1}$ | 23.67% | 97.71% | 0.14% | 1.99% | 0.02% | 0.10% | 0.04% |
| T = 500° C. Feed: PhOH ToS = 5.5 hrs WHSV 1 hr$^{-1}$ | 22.86% | 97.75% | 0.18% | 1.85% | 0.01% | 0.15% | 0.06% |

Example 9

A 1M HoCl$_3$ solution, prepared by dissolving 11.388 g HoCl$_3$ in 30 mL DI H$_2$O, is added dropwise along with tetrapropylammonium hydroxide (45.759 g, from a 40 wt % TPAOH solution) over 15 min into a 600 mL beaker containing an initial 100 mL DI H$_2$O. The solution is stirred at 500 rpm on magnetic stir plate with a 3 inch stir bar. The resulting precipitate is allowed to age in solution for 1 h with stirring, after which it is centrifuged at 5000 rpm for 10 min. The decanted precipitate is placed into an oven, dried at 120° C. for 4 h and calcined at 500° C. for 4 h with a ramp rate of 5° C./min to yield 5 g of product.

Example 10

Catalytic evaluation of the catalyst from Example 9 is carried out using a similar procedure as in Example 2. Test conditions and results are shown in Table 6.

TABLE 6

| Test Conditions | Conversion [mol. %] Phenol | Selectivity [mol. %] | | | | | |
|---|---|---|---|---|---|---|---|
| | | Diphenyl Oxide | OPP | DBF | O-BIPPE | M-BIPPE | P-BIPPE |
| T = 500° C. Feed: PhOH ToS = 1.75 hrs WHSV 1 hr$^{-1}$ | 12.22% | 97.77% | 0.21% | 1.87% | 0.02% | 0.07% | 0.07% |

TABLE 6-continued

| Test Conditions | Conversion [mol. %] Phenol | Diphenyl Oxide | OPP | DBF | O-BIPPE | M-BIPPE | P-BIPPE |
|---|---|---|---|---|---|---|---|
| | | | Selectivity [mol. %] | | | | |
| T = 500° C. Feed: PhOH ToS = 3.75 hrs WHSV 1 hr$^{-1}$ | 12.73% | 97.90% | 0.28% | 1.63% | 0.00% | 0.13% | 0.07% |
| T = 500° C. Feed: PhOH ToS = 5 hrs WHSV 1 hr$^{-1}$ | 12.34% | 97.95% | 0.24% | 1.61% | 0.02% | 0.11% | 0.05% |
| T = 500° C. Feed: PhOH ToS = 7 hrs WHSV 1 hr$^{-1}$ | 12.02% | 97.88% | 0.12% | 1.82% | 0.00% | 0.11% | 0.07% |

Example 11

The synthesis of supported holmium oxychloride is carried out via an incipient wetness impregnation of gamma alumina.
Precursors:
Support: gamma alumina (Saint-Gobain NorPro, 30-60 mesh size, BET=178.9 m$^2$/g) that exhibits an incipient wetness condition of approximately 0.75 mL per 1 g. Solution: holmium(III) chloride hexahydrate (HoCl$_3$.6 H$_2$O) and deionized water (DI water), prepared to c=0.7500 mol/L
Synthesis:
3.75 mL of the solution is added dropwise to 5 g of the support at ambient conditions under vigorous shaking using a shaker plate. The impregnated material is then dried at 150° C. for 1 h, and the impregnation procedure is repeated three more times (total of 4×3.75 mL used for 5 g of carrier) to achieve a high loading of holmium inside the pores of the carrier. The preparation is finished off by calcining the impregnated material in a static air calcination oven using the following protocol: ramp 1° C./min; dwell at T=550° C. for 3 hrs, cool down to room temperature. The chlorine content of the catalyst is assayed by XRF to 4.48 wt. % chlorine.

Example 12

Catalytic evaluation of the catalyst from Example 11 is carried out using a similar procedure as in Example 2. Test conditions and results are shown in Table 7.

Example 13

The synthesis of supported holmium oxychloride is carried out via an incipient wetness impregnation of amorphous silica.
Precursors:
Support: amorphous silica (WR Grace-Davison 57, 30-60 mesh size, BET=275.3 m$^2$/g) that exhibits an incipient wetness condition of approximately 0.90 mL per 1 g. Solution: holmium(III) chloride hexahydrate (HoCl$_3$.6 H$_2$O) and deionized water (DI water), prepared to c=1.25 mol/L.
Synthesis:
4.5 mL of the solution is added dropwise to 5 g of the support at ambient conditions under vigorous shaking using a shaker plate. The impregnated material is then dried at 150° C. for 1 h, and the preparation is finished off by calcining the impregnated material in a static air calcination oven using the following protocol: ramp 1° C./min; dwell at T=550° C. for 3 hrs, step down to room temperature. The chlorine content of the catalyst is assayed by XRF to 2.02 wt. % chlorine.

Example 14

Catalytic evaluation of the catalyst from Example 13 is carried out using a similar procedure as in Example 2. Test conditions and results are shown in Table 8.

TABLE 7

| Test Conditions | Conversion [mol. %] Phenol | Diphenyl Oxide | OPP | DBF | O-BIPPE | M-BIPPE | P-BIPPE |
|---|---|---|---|---|---|---|---|
| | | | Selectivity [mol. %] | | | | |
| T = 500° C. Feed: PhOH ToS = 1.25 hrs WHSV 1 hr$^{-1}$ | 4.57% | 82.05% | 2.32% | 15.22% | 0.06% | 0.17% | 0.19% |
| T = 500° C. Feed: PhOH ToS = 2.25 hrs WHSV 1 hr$^{-1}$ | 4.05% | 83.70% | 1.21% | 14.45% | 0.08% | 0.17% | 0.39% |
| T = 500° C. Feed: PhOH ToS = 3.5 hrs WHSV 1 hr$^{-1}$ | 4.03% | 84.56% | 2.16% | 12.35% | 0.08% | 0.15% | 0.70% |
| T = 500° C. Feed: PhOH ToS = 4.25 hrs WHSV 1 hr$^{-1}$ | 3.20% | 86.04% | 2.86% | 10.42% | 0.09% | 0.00% | 0.58% |

TABLE 8

| Test Conditions | Conversion [mol. %] Phenol | Selectivity [mol. %] | | | | | |
|---|---|---|---|---|---|---|---|
| | | Diphenyl Oxide | OPP | DBF | O-BIPPE | M-BIPPE | P-BIPPE |
| T = 500° C. Feed: PhOH ToS = 1.5 hrs WHSV 1 hr$^{-1}$ | 1.91% | 53.78% | 0.24% | 45.76% | 0.00% | 0.00% | 0.22% |
| T = 500° C. Feed: PhOH ToS = 2.25 hrs WHSV 1 hr$^{-1}$ | 1.86% | 52.16% | 4.21% | 43.27% | 0.00% | 0.00% | 0.36% |
| T = 500° C. Feed: PhOH ToS = 3 hrs WHSV 1 hr$^{-1}$ | 1.49% | 52.09% | 7.17% | 40.36% | 0.00% | 0.00% | 0.39% |
| T = 500° C. Feed: PhOH ToS = 3.75 hrs WHSV 1 hr$^{-1}$ | 1.50% | 51.08% | 1.44% | 47.09% | 0.00% | 0.00% | 0.39% |

Example 15

A preparation of a holmium oxychloride sample is accomplished by setting up a 2-L 3-necked flask with two air-tight addition funnels, pH meter, and argon bubbling into 750 ml of DI H$_2$O at a flow rate of 300 sccm. After purging with argon, an aqueous solution of HoCl$_3$, prepared by dissolving 62.6 g HoCl$_3$ in 165 mL DI H$_2$O, is added dropwise over 0.5 hours along with a controlled addition of aqueous ammonia to maintain the pH constant at 9. The resulting suspension is added to a nitrogen purged centrifuge container, capped, and centrifuged to separate the precipitate from the solution. The liquid is poured off and the containers are placed in a vacuum oven at 80° C. for 16 hours. The dried sample is transferred into a purged quartz tube within a tube furnace where it is treated in flowing 1% oxygen in helium mixture for 5 minutes at room temperature, thermally treated at 500° C. for 3 h, and then cooled to room temperature in flowing nitrogen.

Example 16

Catalytic evaluation of the catalyst from Example 15 is carried out using a similar procedure as in Example 2. Test conditions and results are shown in Table 9.

Example 17

Preparation of 16 wt % Ho supported on ZrO$_2$ via incipient wetness impregnation.

Prior to the impregnation process a hydrous ZrO$_2$ support with BET surface area of 323 m$^2$/g is pre-dried at 120° C. for 4 hours in static air. 16 wt % Ho on ZrO$_2$ catalyst is prepared by two step incipient wetness impregnation of the treated ZrO$_2$ at ambient temperature. A glass beaker is charged with 5 g of pre-dried ZrO$_2$. A 10-ml graduated cylinder is loaded with 0.9207 g of HoCl$_3$.6H$_2$O to yield 8 wt % of Ho and with 1.2 ml of H$_2$O. The support is impregnated with aqueous solution of holmium being added to the ZrO$_2$ in small fractions. After each addition, the support is agitated to break up clumps and uniformly disperse holmium throughout the carrier material. After the first step impregnation, the sample is dried at 110° C. for 4 hours. In the next step the whole process is repeated using 0.9159 g of HoCl$_3$.6H$_2$O to again yield 8 wt % of Ho with 1.2 ml of H$_2$O. The impregnated sample is then treated at 110° C. for 4 hours in flowing air and then at 600° C. for an additional 4 hours a 5° C./min ramp.

Example 18

Catalytic evaluation of the catalyst from Example 17 is carried out using a similar procedure as in Example 2. Test conditions and results are shown in Table 10.

TABLE 9

| Test Conditions | Conversion [mol. %] Phenol | Selectivity [mol. %] | | | | | |
|---|---|---|---|---|---|---|---|
| | | Diphenyl Oxide | OPP | DBF | O-BIPPE | M-BIPPE | P-BIPPE |
| T = 500° C. Feed: PhOH ToS = 1.5 hrs WHSV 1 hr$^{-1}$ | 17.92% | 96.73% | 0.58% | 2.53% | 0.01% | 0.14% | 0.00% |
| T = 500° C. Feed: PhOH ToS = 2.5 hrs WHSV 1 hr$^{-1}$ | 14.96% | 96.44% | 0.36% | 3.01% | 0.02% | 0.17% | 0.00% |
| T = 500° C. Feed: PhOH ToS = 3.75 hrs WHSV 1 hr$^{-1}$ | 12.90% | 96.34% | 0.66% | 2.91% | 0.02% | 0.05% | 0.02% |
| T = 500° C. Feed: PhOH ToS = 4.75 hrs WHSV 1 hr$^{-1}$ | 11.21% | 96.15% | 0.84% | 2.88% | 0.00% | 0.09% | 0.05% |

TABLE 10

| Test Conditions | Conversion [mol. %] Phenol | Selectivity [mol. %] | | | | |
|---|---|---|---|---|---|---|
| | | Diphenyl Oxide | OPP | DBF | O-BIPPE | M-BIPPE | P-BIPPE |
| T = 500° C. Feed: PhOH ToS = 1 hr WHSV 1 hr$^{-1}$ | 2.73% | 93.82% | 0.05% | 6.13% | 0.00% | 0.00% | 0.00% |
| T = 500° C. Feed: PhOH ToS = 2.75 hrs WHSV 1 hr$^{-1}$ | 5.59% | 86.86% | 1.73% | 11.42% | 0.00% | 0.00% | 0.00% |
| T = 500° C. Feed: PhOH ToS = 4 hrs WHSV 1 hr$^{-1}$ | 4.01% | 84.15% | 3.12% | 12.72% | 0.00% | 0.00% | 0.00% |
| T = 500° C. Feed: PhOH ToS = 5 hrs WHSV 1 hr$^{-1}$ | 3.28% | 83.79% | 1.37% | 14.84% | 0.00% | 0.00% | 0.00% |

Example 19

Preparation of 15 wt % Yb Supported on $ZrO_2$ Via Incipient Wetness Impregnation Synthesis:

Prior to the impregnation process a hydrous $ZrO_2$ support with BET surface area of 323 m$^2$/g is pre-dried at 120° C. for 4 hours in static air. 15 wt % Yb on $ZrO_2$ catalyst is prepared by two step incipient wetness impregnation of the treated $ZrO_2$ at ambient temperature. A glass beaker is charged with 5 g of pre-dried $ZrO_2$. A 10-ml graduated cylinder is loaded with a 0.8405 g of $YbCl_3 \cdot 6H_2O$ to yield 7.5 wt % of Yb and with 1.2 ml of $H_2O$. The support is impregnated with aqueous solution of ytterbium being added to the $ZrO_2$ in small fractions. After each addition, the support is agitated to break up clumps and uniformly disperse ytterbium throughout the carrier material. After the first step impregnation, the sample is dried at 110° C. for 4 hours. In the next step the whole process is repeated using 0.8370 g of $YbCl_3 \cdot 6H_2O$ to again yield 7.5 wt % of Yb with 1.2 ml of $H_2O$. The impregnated sample is then treated at 110° C. for 4 hours in flowing air and then at 600° C. for an additional 4 hours at 5° C./min ramp.

Example 20

Catalytic evaluation of the catalyst from Example 19 is carried out using a similar procedure as in Example 2. Test conditions and results are shown in Table 11.

TABLE 11

| Test Conditions | Conversion [mol. %] Phenol | Selectivity [mol. %] | | | | |
|---|---|---|---|---|---|---|
| | | Diphenyl Oxide | OPP | DBF | O-BIPPE | M-BIPPE | P-BIPPE |
| T = 500° C. Feed: PhOH ToS = 1 hr WHSV 1 hr$^{-1}$ | 6.05% | 71.96% | 6.61% | 20.74% | 0.06% | 0.64% | 0.00% |
| T = 500° C. Feed: PhOH ToS = 2.75 hrs WHSV 1 hr$^{-1}$ | 4.08% | 73.59% | 6.35% | 17.09% | 0.00% | 0.99% | 1.98% |
| T = 500° C. Feed: PhOH ToS = 4 hrs WHSV 1 hr$^{-1}$ | 4.03% | 71.42% | 4.67% | 21.49% | 0.00% | 0.72% | 1.69% |
| T = 500° C. Feed: PhOH ToS = 5 hrs WHSV 1 hr$^{-1}$ | 2.97% | 73.63% | 5.57% | 17.87% | 0.00% | 0.78% | 2.15% |

We claim:

1. A method for preparing a diaryl ether, the method comprising dehydrating an aromatic alcohol compound over a dehydration catalyst, wherein the dehydration catalyst is an oxide of a heavy rare earth element.

2. The method of claim 1 wherein the dehydration catalyst further comprises a halogen.

3. The method of claim 2 wherein the halogen is chloride or fluoride ion.

4. The method of any one of claims 1-3 wherein the dehydration catalyst further comprises a binder.

5. The method of any one of claims 1-4 wherein the dehydration catalyst is supported.

6. The method of any one of claims 1-4 wherein the dehydration catalyst is unsupported.

7. The method of any one of claims 1-6 wherein the dehydration of the alcohol is conducted at a temperature from 250 to 600° C.

8. The method of any one of claims 1-7 wherein the alcohol feed is diluted with a diluent.

9. The method of any one of claims 1-8 wherein the aromatic alcohol compound is phenol and the diaryl ether produced is diphenyl oxide.

10. A method for producing a heat transfer fluid, the method comprising:
   preparing a diaryl ether by contacting an aromatic alcohol compound with a dehydration catalyst, wherein the dehydration catalyst is an oxide of a heavy rare earth element;
   isolating the diaryl ether from the dehydration catalyst; and
   mixing the isolated diaryl ether with biphenyl, wherein the mixture forms a eutectic mixture.

* * * * *

UNITED STATES PATENT AND TRADEMARK OFFICE
CERTIFICATE OF CORRECTION

PATENT NO. : 9,150,479 B1
APPLICATION NO. : 14/385917
DATED : October 6, 2015
INVENTOR(S) : David G. Barton et al.

It is certified that error appears in the above-identified patent and that said Letters Patent is hereby corrected as shown below:

In the Claims:

In column 16, lines 64-65, claim no. 4, the text: "The method of any one of claims 1-3 wherein the dehydration catalyst further comprises a binder." should be deleted and replaced with: --The method of claim 1 wherein the dehydration catalyst further comprises a binder.--

In column 16, lines 66-67, claim no. 5, the text: "The method of any one of claims 1-4 wherein the dehydration catalyst is supported." should be deleted and replaced with: --The method of claim 1 wherein the dehydration catalyst is supported.--

In column 17, lines 1-2, claim no. 6, the text: "The method of any one of claims 1-4 wherein the dehydration catalyst is unsupported." should be deleted and replaced with: --The method of claim 1 wherein the dehydration catalyst is unsupported.--

In column 17, lines 3-5, claim no. 7, the text: "The method of any one of claims 1-6 wherein the dehydration of the alcohol is conducted at a temperature from 250 to 600°C." should be deleted and replaced with: --The method of claim 1 wherein the dehydration of the alcohol is conducted at a temperature from 250 to 600°C.--

In column 17, lines 6-7, claim no. 8, the text: "The method of any one of claims 1-7 wherein the alcohol feed is diluted with a diluent." should be deleted and replaced with: --The method of claim 1 wherein the alcohol feed is diluted with a diluent.--

In column 17, lines 8-10, claim no. 9, the text: "The method of any one of claims 1-8 wherein the aromatic alcohol compound is phenol and the diaryl ether produced is diphenyl oxide." should be deleted and replaced with: --The method of claim 1 wherein the aromatic alcohol compound is phenol and the diaryl ether produced is diphenyl oxide.--

Signed and Sealed this
Fourteenth Day of June, 2016

Michelle K. Lee
*Director of the United States Patent and Trademark Office*